(12) United States Patent
Hayashi et al.

(10) Patent No.: US 10,739,359 B2
(45) Date of Patent: Aug. 11, 2020

(54) BLOOD CONDITION ANALYSIS DEVICE, BLOOD CONDITION ANALYSIS SYSTEM, BLOOD CONDITION ANALYSIS METHOD, AND BLOOD CONDITION ANALYSIS PROGRAM FOR CAUSING COMPUTER TO IMPLEMENT THE METHOD

(71) Applicant: Sony Corporation, Tokyo (JP)

(72) Inventors: Yoshihito Hayashi, Chiba (JP); Marcaurele Brun, Tokyo (JP); Kenzo Machida, Kanagawa (JP)

(73) Assignee: Sony Corporation, Tokyo (JP)

( * ) Notice: Subject to any disclaimer, the term of this patent is extended or adjusted under 35 U.S.C. 154(b) by 876 days.

(21) Appl. No.: 15/302,562

(22) PCT Filed: Feb. 19, 2015

(86) PCT No.: PCT/JP2015/054566
§ 371 (c)(1),
(2) Date: Oct. 7, 2016

(87) PCT Pub. No.: WO2015/159583
PCT Pub. Date: Oct. 22, 2015

(65) Prior Publication Data
US 2017/0023597 A1    Jan. 26, 2017

(30) Foreign Application Priority Data

Apr. 17, 2014  (JP) ................................. 2014-085513

(51) Int. Cl.
*G01N 33/86* (2006.01)
*G01N 33/49* (2006.01)
*G01N 27/02* (2006.01)

(52) U.S. Cl.
CPC ............. *G01N 33/86* (2013.01); *G01N 27/02* (2013.01); *G01N 33/49* (2013.01); *G01N 33/4905* (2013.01)

(58) Field of Classification Search
CPC ...................................................... G01N 33/86
USPC ......................................................... 702/19
See application file for complete search history.

(56) References Cited

U.S. PATENT DOCUMENTS

| | | | |
|---|---|---|---|
| 5,686,309 A | 11/1997 | Frank et al. | |
| 10,234,469 B2 | 3/2019 | Hayashi et al. | |
| 2008/0214978 A1* | 9/2008 | Sparks | A61M 1/1656 604/5.01 |
| 2010/0292932 A1 | 11/2010 | Won | |
| 2012/0035450 A1 | 2/2012 | Hayashi | |
| 2014/0014509 A1 | 1/2014 | Yan et al. | |
| 2016/0018346 A1 | 1/2016 | Hayashi et al. | |
| 2017/0030934 A1 | 2/2017 | Hayashi et al. | |

FOREIGN PATENT DOCUMENTS

| | | |
|---|---|---|
| CN | 1914511 A | 2/2007 |
| CN | 101542292 A | 9/2009 |
| CN | 101784294 A | 7/2010 |
| CN | 102099683 A | 6/2011 |
| CN | 102768179 A | 11/2012 |
| CN | 103471980 A | 12/2013 |
| EP | 1 862 792 A2 | 12/2007 |
| EP | 2 098 867 A2 | 9/2009 |
| EP | 2348319 A1 | 7/2011 |
| EP | 2 375 244 A1 | 10/2011 |
| EP | 3133390 A1 | 2/2017 |
| GB | 2260407 A | 4/1993 |
| JP | 10-123140 A | 5/1998 |
| JP | 2000-503772 A | 3/2000 |
| JP | 2002-542452 A | 12/2002 |
| JP | 2009-243955 A | 10/2009 |
| JP | 2010-181400 A | 8/2010 |
| JP | 2012-147451 A1 | 7/2014 |
| WO | WO 1997/26528 A1 | 7/1997 |
| WO | WO 99/47907 A1 | 9/1999 |
| WO | WO 2005/054847 A1 | 6/2005 |
| WO | WO 2006/129703 A1 | 12/2006 |
| WO | WO 2011/159820 A1 | 12/2011 |
| WO | WO 2013/067536 A1 | 5/2013 |
| WO | WO 2013/153735 A1 | 10/2013 |
| WO | WO 2014/036484 A1 | 3/2014 |
| WO | WO 2015/159516 A1 | 10/2015 |

OTHER PUBLICATIONS

Hayashi et al., The effects of erythrocyte deformability upon hematocrit assessed by the conductance method., Physics in Medicine and Biology, vol. 54, 2009, pp. 2395-2405.
Irimajiri et al., Zenketsu no Yuden Kyodo kara Mita Sekkekkyu Gyoshu (Renzen Keisei, Biotechnology, 2000, vol. 78, No. 5, pp. 162-165.
Extended European Search Report dated Sep. 22, 2017 in connection with European Application No. 15779518.8.
Communication pursuant to Article 94(3) issued May 15, 2018 in connection with EP 15779518.8.
Japanese Office Action dated Apr. 10, 2018 in connection with Japanese Application No. 2014-085511 and English translation thereof.
Chinese Office Action dated Jul. 11, 2018 in connection with Chinese Application No. 2015800188598 and English translation thereof.
Chinese Office Action dated Jul. 20, 2018 in connect with Chinese Application No. 2015800190193 and English translation thereof.

(Continued)

*Primary Examiner* — Jerry Lin
(74) *Attorney, Agent, or Firm* — Wolf, Greenfield & Sacks, P.C.

(57) ABSTRACT

To provide a technology that allows for simple and highly accurate evaluation of the condition of blood. Provided is a blood condition analysis device, for analyzing the condition of a blood sample having added thereto at least one kind of drug selected from the group consisting of anticoagulation treatment cancelling agents, coagulation activators, anticoagulants, platelet activators, and antiplatelet agents, the device including a drug dosage control unit for controlling the dosage of the drug to be added to the blood sample on the basis of the hematocrit and/or hemoglobin content of the blood sample.

13 Claims, 4 Drawing Sheets

(56) References Cited

OTHER PUBLICATIONS

Atsuko Narita et al., Error factor in blood clotting inspection, first report, influence caused by specimen extraction method, medical inspection, 1995, vol. 44(5), 890-894.
International Search Report and Written Opinion and English translation thereof dated Apr. 7, 2015 in connection with International Application No. PCT/JP2015/054566.
International Search Report and Written Opinion dated Jun. 22, 2015 in connection with International Application No. PCT/JP2015/001989.
International Preliminary Report on Patentability and English translation thereof dated Oct. 27, 2016 in connection with International Application No. PCT/JP2015/054566.
International Preliminary Report on Patentability dated Oct. 27, 2016 in connection with International Application No. PCT/JP2015/001989.

\* cited by examiner

BLOOD CONDITION ANALYSIS DEVICE, BLOOD CONDITION ANALYSIS SYSTEM, BLOOD CONDITION ANALYSIS METHOD, AND BLOOD CONDITION ANALYSIS PROGRAM FOR CAUSING COMPUTER TO IMPLEMENT THE METHOD

CROSS-REFERENCE TO RELATED APPLICATIONS

This application claims the benefit under 35 U.S.C. § 371 as a U.S. National Stage Entry of International Application No. PCT/JP2015/054566, filed in the Japanese Patent Office as a Receiving Office on Feb. 19, 2015, which claims priority to Japanese Patent Application Number JP2014-085513, filed in the Japanese Patent Office on Apr. 17, 2014, each of which is hereby incorporated by reference in its entirety.

TECHNICAL FIELD

This technology relates to a blood condition analysis device. More specifically, it relates to a device for analyzing the condition of a blood sample having added thereto at least one kind of drug selected from the group consisting of anticoagulation treatment canceling agents, coagulation activators, anticoagulants, platelet activators, and antiplatelet agents, a blood condition analysis system, a blood condition analysis method, and a blood condition analysis program for causing a computer to implement the method.

BACKGROUND ART

Clinical methods for analyzing the condition of blood include blood coagulation tests, for example. As general blood coagulation tests, blood coagulation tests represented by the prothrombin time (PT) and the activated partial thromboplastin time (APTT) are known. According to these methods, a blood sample is centrifuged, and a protein that is contained in the resulting blood plasma and involved in the coagulation reaction is analyzed. This field has already been technically established, and it has been believed that the needs in the medical front are almost satisfied.

However, in the perioperative (acute stage) treatment, for example, which requires promptness, in order to satisfy the needs of testing the patient's comprehensive disease states of coagulation accurately in a simple manner, the above methods are insufficient. Specifically, for example, in large-scale surgical operations such as heart surgery accompanied by extracorporeal circulation using an artificial heart-lung machine, serious traumatotherapy, and liver transplantation, in addition to surgical bleeding, bleeding resulting from abnormal coagulation may continue. In spite of this, in conventional coagulation tests, cell components such as platelets and erythrocytes, which play important roles in the in-vivo coagulation reaction, are removed by centrifugation. Therefore, it often happens that the test results are inconsistent with the actual clinical disease states.

In addition, the disease states of coagulation in the patient significantly vary through the perioperative period, and a bleeding tendency often turns into a thrombosis tendency. However, PT and APTT are tests for bleeding tendencies, and a high-sensitivity testing method for thrombosis tendencies has not yet been established.

As a comprehensive coagulation test in the acute stage, thromboelastometry, which dynamically measures changes in viscoelasticity accompanying the process of blood coagulation, has been commercialized by European and American companies under TEG® and ROTEM®. However, with respect to these products, there are issues such as (1) the measurement has not been automated, and the test results depend on the measurer's manipulation, (2) the measurement is susceptible to vibration, (3) the quality control (QC) procedure is complicated, and the reagent therefor is expensive, (4) the interpretation of output signals (thromboelastogram) requires skill, etc. These are considered to be the primary cause that hinders sufficient spread. Therefore, under the present circumstances, even for patients who would not need blood transfusion if subjected to a comprehensive coagulation test, blood preparations are often used for preventive and experimental purposes. This not only increases the risks of infectious diseases but also wastes blood preparations and increases the medical cost.

In recent years, a technology for evaluating the degree of blood coagulation accurately in a simple manner has been developed. For example, Patent Document 1 discloses a technology for obtaining the information about blood coagulation from the permittivity of blood, and describes "a blood coagulation system analysis device, including: a pair of electrodes; an application means for applying an alternating voltage to the pair of electrodes at predetermined time intervals; a measurement means for measuring the permittivity of blood placed between the pair of electrodes; and an analysis means for, using the blood permittivity measured at the time intervals after the cancellation of the effect of an anticoagulant on the blood, analyzing the degree of action of the blood coagulation system."

As a blood specimen in this method, generally, blood collected from the vein using an anticoagulant such as citric acid is used. Immediately before the start of measurement, the anticoagulation effect is canceled using an anticoagulation treatment canceling agent such as an aqueous calcium chloride solution, and the measurement is performed with the blood coagulation reaction being promoted.

CITATION LIST

Patent Document

Patent Document 1: JP 2010-181400 A

Non-Patent Document

Non-Patent Document 1: Phys. Med. Biol. 54 (2009), 2395-2405

SUMMARY OF THE INVENTION

Problems to be Solved by the Invention

As described above, technologies for evaluating the condition of blood have been progressing day by day. Meanwhile, in recent years, it has turned out that artifacts are caused by certain factors aside from the patient's clinical conditions.

Thus, a main object of the present technology is to provide a technology that allows for simple and highly accurate evaluation of the condition of blood.

Solutions to Problems

In order to solve the above problems, the present inventors have conducted extensive research about the cause of artifacts in the blood condition evaluation results. As a result, they have found the following: due to the excluded volume effect of blood cell components in the blood, the drug used for measurement is concentrated in the blood plasma, and the blood condition evaluation results are significantly affected by such concentration. The present technology has thus been accomplished.

That is, the present technology firstly provides a blood condition analysis device, for analyzing the condition of a blood sample having added thereto at least one kind of drug selected from the group consisting of anticoagulation treatment canceling agents, coagulation activators, anticoagulants, platelet activators, and antiplatelet agents, the device including a drug dosage control unit for controlling the dosage of the drug to be added to the blood sample on the basis of the hematocrit and/or hemoglobin content of the blood sample.

Further, the drug dosage control unit may include a drug dosage determination unit for determining the dosage of the drug to be added to the blood sample on the basis of the hematocrit and/or hemoglobin content of the blood sample.

In addition, the drug dosage control unit may include a drug dilution unit for diluting the drug.

Further, the blood condition analysis device may include a drug dilution unit for diluting the drug on the basis of the dosage determined by the drug dosage determination unit.

The blood condition analysis device according to the present technology may further include a drug concentration detection unit for detecting the concentration of the drug to be added to the blood sample.

In addition, the blood condition analysis device according to the present technology may further include an erythrocyte quantitative evaluation unit for determining the hematocrit and/or hemoglobin content on the basis of an electrical characteristic of the blood sample.

Further, the blood condition analysis device according to the present technology may further include a blood coagulation evaluation unit for evaluating the degree of blood coagulation on the basis of an electrical characteristic of the blood sample.

Furthermore, the blood condition analysis device according to the present technology may further include a measurement unit for measuring electrical characteristics of the blood sample.

In the blood condition analysis device according to the present technology, the red blood cell quantitative evaluation unit and the blood coagulation evaluation unit may be provided in the same device.

The present technology secondly provides a blood condition analysis system, including:

an electrical characteristic measurement device including a measurement unit for measuring electrical characteristics of a blood sample; and a blood condition analysis device for analyzing the condition of the blood sample having added thereto at least one kind of drug selected from the group consisting of anticoagulation treatment canceling agents, coagulation activators, anticoagulants, platelet activators, and antiplatelet agents, the device including a drug dosage control unit for controlling the dosage of the drug to be added to the blood sample on the basis of the hematocrit and/or hemoglobin content of the blood sample.

The blood condition analysis system according to the present technology may further include a server for storing measurement results from the electrical characteristic measurement device and/or analysis results from the blood condition analysis device.

In this case, the server may be connected to the electrical characteristic measurement device and/or the blood condition analysis device through a network.

The present technology further provides a blood condition analysis method, for analyzing the condition of a blood sample having added thereto at least one kind of drug selected from the group consisting of anticoagulation treatment canceling agents, coagulation activators, anticoagulants, platelet activators, and antiplatelet agents, the method including a drug dosage control step of controlling the dosage of the drug to be added to the blood sample on the basis of the hematocrit and/or hemoglobin content of the blood sample.

The present technology further provides a blood condition analysis program, for use in the analysis of the condition of a blood sample having added thereto at least one kind of drug selected from the group consisting of anticoagulation treatment canceling agents, coagulation activators, anticoagulants, platelet activators, and antiplatelet agents, the program causing a computer to implement a drug dosage control function of controlling the dosage of the drug to be added to the blood sample on the basis of the hematocrit and/or hemoglobin content of the blood sample.

Effects of the Invention

The present technology allows for simple and highly accurate evaluation of the condition of blood. Incidentally, the effects described herein are not necessarily limited, and may be any of the effects described in the present technology.

MODE FOR CARRYING OUT THE INVENTION

Hereinafter, best modes for carrying out the present technology will be described with reference to the drawings. Incidentally, the embodiments described hereinafter show examples of typical embodiments of the present technology, and do not narrow the interpretation of the scope of the present technology. Incidentally, the description will be given in the following order.

1. Blood condition analysis device 1
(1) Drug dosage control unit 11
(a) Drug dosage determination unit 111
(b) Drug dilution unit 112
(2) Drug concentration detection unit 12
(3) Erythrocyte quantitative evaluation unit 13
(4) Blood coagulation evaluation unit 14
(5) Measurement unit 15

(6) Storage unit 16
(7) Blood sample
(8) Blood condition analysis flow using blood condition analysis device 1
2. Blood condition analysis system 10
(1) Electrical characteristic measurement device 101
(2) Blood condition analysis device 1
(3) Server 102
(4) Display unit 103
(5) User interface 104
3. Blood condition analysis method
(1) Drug dosage control step I
(2) Drug concentration detection step II
(3) Erythrocyte quantitative evaluation step III
(4) Blood coagulation evaluation step IV
(5) Measurement step V
(6) Storage step VI
4. Blood condition analysis program
1. Blood Condition Analysis Device 1

Figure 1:
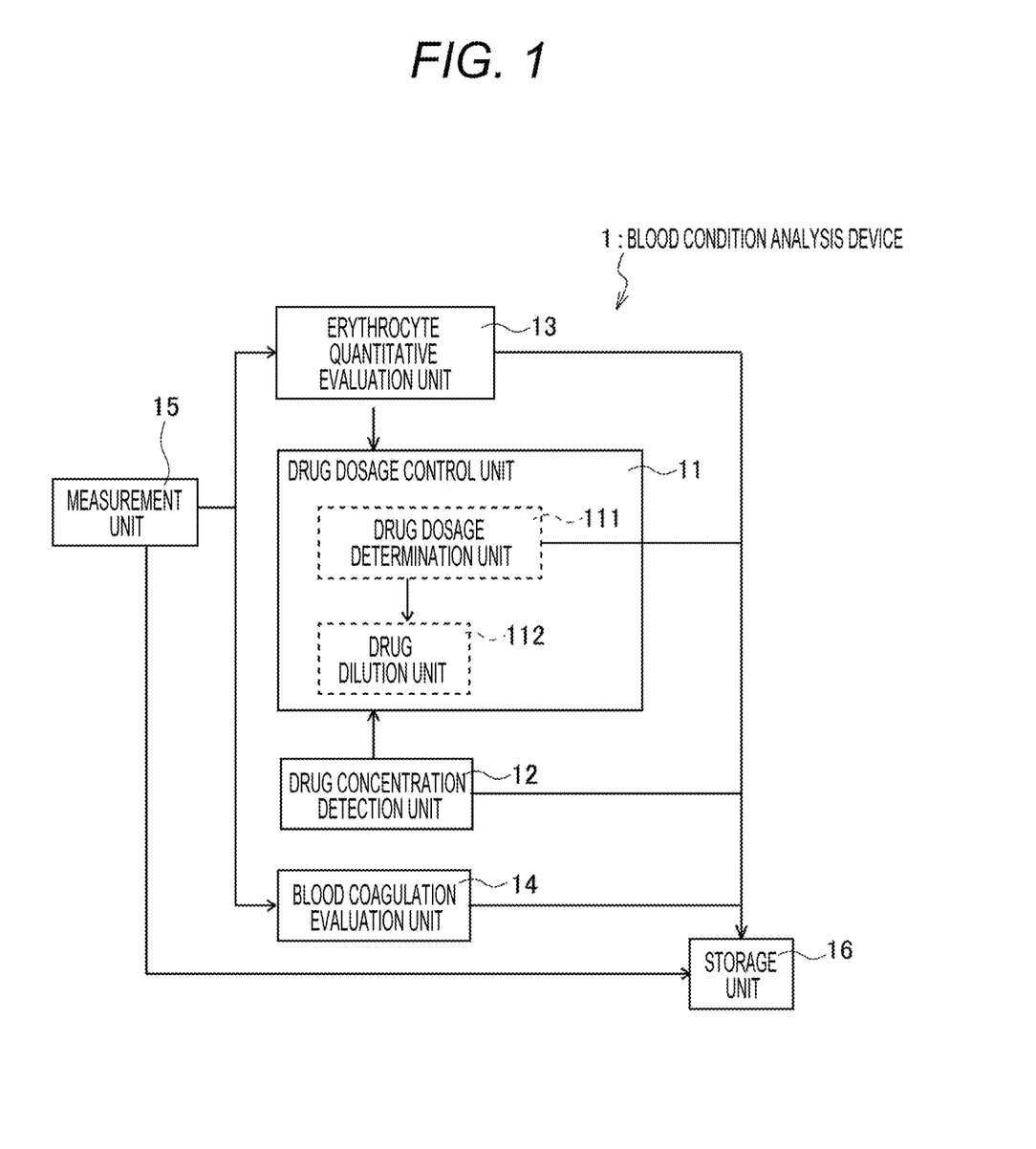
FIG. 1 is a schematic diagram schematically showing the concept of a blood condition analysis device 1 according to the present technology.

FIG. 1 is a schematic diagram schematically showing the concept of a blood condition analysis device 1 according to the present technology (hereinafter sometimes referred to as "device 1"). The blood condition analysis device 1 according to the present technology is a device for analyzing the condition of a blood sample having added thereto at least one kind of drug selected from the group consisting of anticoagulation treatment canceling agents, coagulation activators, anticoagulants, platelet activators, and antiplatelet agents (hereinafter referred to as "the drug"), and includes at least a drug dosage control unit 11. In addition, as necessary, the device may also include a drug dosage determination unit 111, a drug dilution unit 112, a drug concentration detection unit 12, an erythrocyte quantitative evaluation unit 13, a blood coagulation evaluation unit 14, a measurement unit 15, a storage unit 16, and the like.

As the drug, for example, it is possible to freely select and use at least one kind selected from the group consisting of anticoagulation treatment canceling agents such as calcium chloride, calcium sulfate, calcium carbonate, and calcium acetate (i.e., these are calcium salts); coagulation activators such as tissue factors, contact factors, ellagic acid, kaolin, celite, thrombin, and batroxobin; anticoagulants such as citric acid, heparin, hirudin, EDTA, direct thrombin inhibitors, and activated X factor inhibitors; platelet activators such as collagen, arachidonic acid, ADP, and thrombin; and antiplatelet agents such as acetylsalicylic acid (aspirin), prostaglandin, thromboxane synthetase inhibitors, thienopyridine derivatives (ticlopidine hydrochloride, clopidogrel, prasugrel, etc.), PDE3 inhibitors, 5-serotonin receptor 2 antagonists, and GPIIb/IIIa inhibitors.

Hereinafter, each unit will be described in detail.

(1) Drug Dosage Control Unit 11

In the drug dosage control unit 11, on the basis of the hematocrit and/or hemoglobin content of a blood sample, the dosage of the drug to be added to the blood sample is controlled.

As described above, when the condition of blood is evaluated from the blood sample having added thereto various drugs, such drugs used at the time of measurement are concentrated in the blood plasma due to the excluded volume effect of blood cell components in the blood. That is, in the case where blood plasma resulting from the removal of blood cell components is used as a sample, the effective concentration of the drug used for the test is determined only by the amount of blood sample and the amount of drug added. However, in the case where a blood sample containing blood cell components is used, the proportions of blood cell components and blood plasma components are different in every specimen, and, therefore, the effective concentration of the drug added is different in every specimen. Further, as shown in the Examples below, it has been found that in the present technology, even in the case of using the same blood specimen, the parameter that indicates the blood coagulation ability varies depending on the added drug concentration in the blood plasma. That is, it has been found that errors occur in the blood coagulation evaluation results depending on the amount of drug added, the proportion of blood plasma in the blood specimen, and the like. Thus, in the present technology, the dosage of the drug to be added to the blood sample is controlled on the basis of the hematocrit and/or hemoglobin content of the blood sample, thereby eliminating artifacts caused by changes in the concentration of the drug in the blood plasma, making it possible to perform more accurate evaluation.

A blood sample having a high hematocrit and/or hemoglobin content relatively has a small amount of blood plasma, whereas a blood sample having a low hematocrit and/or hemoglobin content has relatively a large amount of blood plasma. That is, the amount of blood plasma shows a negative correlation with the hematocrit and/or hemoglobin content of the blood sample. Utilizing this correlation, the drug dosage control unit 11 controls the dosage of the drug to be added to the blood sample.

As the hematocrit and/or hemoglobin content of the blood sample, a measured value previously determined by a different device or method may be used, and it is also possible that the device 1 includes the erythrocyte quantitative evaluation unit 13 described below, and the hematocrit and/or hemoglobin content obtained by this erythrocyte quantitative evaluation unit 13 is used.

(a) Drug Dosage Determination Unit 111

The drug dosage control unit 11 may include a drug dosage determination unit 111. In the drug dosage determination unit 111, on the basis of the hematocrit and/or hemoglobin content of the blood sample, the dosage of the drug to be added to the blood sample is determined.

The drug dosage determination unit 111 is not indispensable in the blood condition analysis device 1 according to the present technology. For example, it is also possible that the drug dosage corresponding to each hematocrit and/or hemoglobin content is previously specified, whereby, at the time when the hematocrit and/or hemoglobin content is input to the device 1, or alternatively, at the time when the hematocrit and/or hemoglobin content is measured by the erythrocyte quantitative evaluation unit 13 described below, the drug dosage control unit 11 automatically controls the drug concentration without the determination step.

The specific determination method in the drug dosage determination unit 111 is not particularly limited as long as the effects of the present technology are not impaired, and a known determination method may be freely selected and used. For example, it is possible to employ a method in which the amount of blood plasma is calculated from the hematocrit and/or hemoglobin content, and the drug dosage determination unit 111 automatically determines the drug dosage corresponding to the calculated amount of blood plasma so as to provide the effective amount of drug optimal for the kind of drug or the blood condition to be evaluated.

(b) Drug Dilution Unit 112

The drug dosage control unit 11 may include a drug dilution unit 112. In the drug dilution unit 112, the drug is diluted. The drug dilution unit 112 is not indispensable in the blood condition analysis device 1 according to the present technology. For example, the amount of drug controlled by the drug dosage control unit 11 on the basis of the hematocrit and/or hemoglobin content may be directly added. However, when the drug dilution unit 112 is provided, it is possible to control only the drug concentration, while maintaining the amount of added liquid constant. By maintaining the amount of added liquid constant, measurement errors due to the difference in the total amount between samples to be measured, for example, can be eliminated.

Solvents used for dilution are not particularly limited as long as the effects of the present technology are not impaired, and may be freely selected according to the kind of drug used, the kind of solvent used in the drug, and the like.

In the drug dilution unit 112, for example, it is also possible that the drug concentration corresponding to each hematocrit and/or hemoglobin content is previously specified, whereby the diluent is automatically added at the time when the hematocrit and/or hemoglobin content is input to the device 1, or alternatively, at the time when the hematocrit and/or hemoglobin content is measured by the erythrocyte quantitative evaluation unit 13 described below. In addition, it is also possible that the drug is diluted on the basis of the drug dosage determined by the drug dosage determination unit 111.

(2) Drug Concentration Detection Unit 12

In the drug concentration detection unit 12, the concentration of the drug to be added to the blood sample is detected. In the blood condition analysis device 1 according to the present technology, the effective concentration of the drug in the blood sample is controlled to be the optimum density by the drug dosage control unit 11, and thus the drug concentration detection unit 12 is not indispensable. However, when the drug concentration detection unit 12 is provided, and the actual concentration of the drug to be added to the blood sample is checked, the measurement accuracy can be further improved.

In the drug concentration detection unit 12, the specific concentration of the drug may be measured. However, it is also possible to detect only whether the concentration of the drug actually added is within the range that does not affect changes in the condition of blood.

In the drug concentration detection unit 12, the method for detecting the drug concentration is not particularly limited, and a known method may be freely selected and used. For example, the drug concentration can be detected by optical detection or electrical detection. More specifically, for example, it is possible that the diluted drug is once dispensed into a cuvette for optical measurement, and the absorbance is determined to measure the drug concentration. Here, in the case where a protein, such as heparinase, is contained as the drug, the absorbance of an aromatic amino acid in the protein (tyrosine, tryptophan, phenylalanine, etc.) may be utilized, and a wavelength of 280 nm may be selected, for example. In addition, in the case where such an aromatic amino acid is not contained in the reagent itself, the aromatic amino acid may be previously added to a high-concentration drug solution or a diluent (or low-concentration drug solution), whereby the reagent concentration can be detected by absorbance measurement. Alternatively, the reagent concentration may also be detected by fluorescence measurement using a fluorescent label or the like in place of aromatic amino acids. In this case, as the fluorescent label used, those that do not affect blood coagulation or platelet function are preferable.

(3) Erythrocyte Quantitative Evaluation Unit 13

In the erythrocyte quantitative evaluation unit 13, the hematocrit and/or hemoglobin content is evaluated on the basis of an electrical characteristic of the blood sample. The erythrocyte quantitative evaluation unit 13 is not indispensable in the blood condition analysis device 1 according to the present technology. For example, it is also possible that the hematocrit and/or hemoglobin content of the blood sample is previously measured by a different device or method. However, when the erythrocyte quantitative evaluation unit 13 is provided, the measurement of the hematocrit and/or hemoglobin content and the control of the dosage of the drug to be added to the blood sample based on the obtained hematocrit and/or hemoglobin content can be performed in the same device. As a result, it is possible to achieve the reduction of analysis cost, the shortening of analysis time, and the like.

In the case where there is an external electrical characteristic measurement device, or the blood condition analysis device 1 according to the present technology includes the measurement unit 15 described below, as the electrical characteristic of the blood sample, the raw data measured by the measurement unit 15 may be directly used. Alternatively, it is also possible to use data prepared by removing noise from the raw data.

Examples of electrical characteristics of a blood usable in the erythrocyte quantitative evaluation unit 13 include permittivity, impedance, admittance, capacitance, conductance, conductivity, and phase angle. These electrical characteristics can be mutually converted by the equations shown in the following Table 1. Therefore, for example, the evaluation results of evaluating the hematocrit and/or hemoglobin content using the results of measuring the permittivity of a blood sample are the same as the evaluation results in the case of using the results of measuring the impedance of the same blood sample. Many of these electrical quantities and property values can be described using complex numbers, whereby the conversion equations can be simplified.

TABLE 1

<Main electrical quantities and property values mutually convertible>

| Electrical quantities and property values | Symbol | Complex representation |
|---|---|---|
| Voltage | V | $V^* = \|V\|\exp j(\omega t + \phi)$ |
| Current | I | $I^* = \|I\|\exp j(\omega t + \varphi)$ |
| Impedance | Z | $Z^* = R + jX$ (R: Resistance, X: Reactance) |
| Admittance | Y | $Y^* = G + jB$ (G: Conductance, B: Susceptance) |
| Capacitance | C | $C^* = C - jG/\omega$ |
| Conductance | G | $G^* = G + j\omega C$ |
| Loss tangent (dielectric loss tangent) | D or $\tan\delta$ | |
| Loss angle | $\delta$ | |
| Phase angle | $\theta$ | |
| Q-value | Q | |
| Permittivity | $\varepsilon$ | $\varepsilon^* = \varepsilon - j\, \kappa/\omega\varepsilon_0$ |
| Conductivity | $\kappa$ | $\kappa^* = \kappa + j\, \omega\varepsilon_0\varepsilon$ |

<Equations to associate the electrical quantities and property $Z^* = V^*/I^*$
$\theta = \phi - \varphi$
$Y^* = 1/Z^*$
$C = B/\omega$ TABLE 1-continued <Main electrical quantities and property
values mutually convertible>

$D = \tan\delta = G/\omega C = 1/Q$
$\varepsilon^* = C^*/C_0$
$\kappa^* = j\,\omega\varepsilon_0\varepsilon^*$ $\omega$: Angular frequency
$\varepsilon_0$: Permittivity in vacuum (constant)
$C_0$: Constant depending on the measurement device, etc.
Values indicated with *complex numbers As the electrical characteristic used for the evaluation in the erythrocyte quantitative evaluation unit 13, electrical characteristics at any frequency are usable. However, in the present technology, it is particularly preferable to evaluate the hematocrit and/or hemoglobin content from an electrical characteristic of the blood sample at a frequency of 2 to 25 MHz, and it is more preferable to evaluate the hematocrit and/or hemoglobin content from an electrical characteristic of the blood sample at a frequency of 2 to 10 MHz. This is because electrical characteristics of a blood sample at a frequency of 2 to 25 MHz are less likely to be affected by erythrocyte rouleaux formation, and, in addition, the variation is small until the blood coagulation reaction reaches a certain level, showing correlations with the hematocrit and hemoglobin content obtained by the general, conventional blood test. In addition, at a frequency higher than 10 MHz, the electrical response of blood is weak, and the influence of noise is relatively strong. Therefore, by using electrical characteristics at a frequency of 10 MHz or less, the evaluation can be performed more accurately.

Incidentally, as the electrical characteristic of blood used in the erythrocyte quantitative evaluation unit 13, it is preferable to use an electrical characteristic as early as possible after the start of measurement. Specifically, it is preferable to use an electrical characteristic within 3 minutes after canceling the anticoagulation by the anticoagulant. This is because within 3 minutes after canceling the anticoagulation, the influences of the rouleaux formation or coagulation of blood can be minimized. In addition, in the case of measurement with a coagulation activator added, the time until the start of blood coagulation is short. Therefore, it is preferable to use an electrical characteristic within 1 minute after canceling anticoagulation.

(4) Blood Coagulation Evaluation Unit 14

In the blood coagulation evaluation unit 14, the degree of blood coagulation is evaluated on the basis of an electrical characteristic of the blood sample. The blood coagulation evaluation unit 14 is not indispensable in the blood condition analysis device 1 according to the present technology. For example, it is also possible that the blood coagulation evaluation results are previously obtained by a different device or method.

Electrical characteristics of blood usable in the blood coagulation evaluation unit 14 are the same as the electrical characteristics usable in the erythrocyte quantitative evaluation unit 13 described above, and thus the description will be omitted herein.

As the electrical characteristic used for the evaluation in the blood coagulation evaluation unit 14, electrical characteristics at any frequency are usable. However, it is particularly preferable to evaluate the degree of blood coagulation from an electrical characteristic of the blood sample at a frequency of 1 kHz to 50 MHz, and it is more preferable to evaluate the degree of blood coagulation from an electrical characteristic of the blood sample at a frequency 3 MHz to 15 MHz. This is because changes in the electrical characteristic due to blood coagulation can be seen at a frequency of 1 kHz to 50 MHz, and changes in the electrical characteristic are more prominent at a frequency of 3 MHz to 15 MHz.

The blood condition analysis device 1 according to the present technology may also include, in addition to the drug dosage control unit 11, the erythrocyte quantitative evaluation unit 13 and the blood coagulation evaluation unit 14. When the device 1 includes these units, the series of processes, including first evaluating the hematocrit and/or hemoglobin content on the basis of the electrical characteristic of the blood sample, then controlling the dosage of the drug to be added to the blood sample on the basis of the obtained hematocrit and/or hemoglobin content, and evaluating the degree of blood coagulation on the basis of the electrical characteristic of the blood sample having added thereto an optimal amount of drug, can be performed in one device. As a result, it is possible to achieve the reduction of analysis cost, the shortening of analysis time, and the like.

In the case where the blood condition analysis device 1 according to the present technology includes both the erythrocyte quantitative evaluation unit 13 and the blood coagulation evaluation unit 14, the electrical characteristics used for evaluation in the two evaluation units may be electrical characteristics at the same frequency. However, it is also possible that the hematocrit and/or hemoglobin content is determined on the basis of the electrical characteristic at a first frequency in the erythrocyte quantitative evaluation unit 13, and the degree of blood coagulation is evaluated on the basis of the electrical characteristic of the blood sample at a second frequency different from the first frequency in the blood coagulation evaluation unit 14. For example, as described above, the preferred frequency of the electrical characteristic used for evaluation is different between the erythrocyte quantitative evaluation unit 13 and the blood coagulation evaluation unit 14. Therefore, by using the electrical characteristic at a frequency band more suitable for each unit, the evaluation can be performed more accurately.

(5) Measurement Unit 15

In the measurement unit 15, an electrical characteristic of the blood sample is measured. In the blood condition analysis device 1 according to the present technology, the measurement unit 15 is not indispensable, and it is also possible to use data measured using an external electrical characteristic measurement device.

The measurement unit 15 may include one or more blood sample holders. In the blood condition analysis device 1, such a blood sample holder is not indispensable. For example, it is also possible that the measurement unit 15 is designed to a shape that allows for the installation of a known cartridge-type or like measurement container, for example.

In the case where the measurement unit 15 includes a blood sample holder, the shape of the blood sample holder is not particularly limited as long as the blood sample to be measured can be contained in the measurement unit 15, and may be freely designed. For example, it is possible that one or more cells provided on the substrate serve as blood sample holders, or one or more containers serve as blood sample holders.

In the case where one or more containers are used as blood sample holders, their shape is also not particularly limited either. As long as the blood sample to be measured can be held, the shape may be freely designed according to the condition of the blood sample, the measurement method, and the like, examples thereof including a cylindrical shape, a polygonal cylindrical shape having a polygonal cross-section (triangular, rectangular, or more), a conical shape, a polygonal conical shape having a polygonal cross-section (triangular, rectangular, or more), and a shape that combines one or two or more kinds of them.

In addition, the material to form the container is not particularly limited either, and may be freely selected without affecting the condition of the blood sample to be measured, the purpose of measurement, and the like. In the present technology, in terms of the ease of processing and forming, it is particularly preferable that the container is made of a resin. The kind of resin usable in the present technology is not particularly limited either, and one or two or more kinds of resins applicable to hold a blood sample may be freely selected and used. Examples thereof include hydrophobic and insulating polymers, copolymers, and blend polymers of polypropylene, polymethyl methacrylate, polystyrene, acrylic, polysulfone, polytetrafluoroethylene, and the like. In the present technology, among them, it is particularly preferable that at least one kind of resin selected from polypropylene, polystyrene, acrylic, and polysulfone is used to form the blood sample holder. This is because these resins have the property of low coagulant activity on blood.

It is preferable that the blood sample holder is configured to be hermetically sealable with a blood sample being contained therein. However, the configuration does not have to be hermetic as long as the blood sample can be retained for a period of time required to measure the electrical characteristic thereof, and also the measurement is not affected.

Specific methods for introducing a blood sample to the blood sample holder and hermetically sealing the same are not particularly limited, and a blood sample can be introduced by any method according to the shape of the blood sample holder. For example, it is possible to employ a method in which the blood sample holder is provided with a lid portion, and, after introducing a blood sample using a pipet or the like, the lid portion is closed to hermetically seal the holder, a method in which an injection needle is pierced through the outer surface of the blood sample holder, then a blood sample is injected, and subsequently the injection needle penetrating part is blocked with grease or the like to hermetically seal the holder, or the like The measurement unit 15 may include one or more application units. In the blood condition analysis device 1, such an application unit is not indispensable. For example, it is also possible that the device is designed to allow an electrode to be externally inserted into the blood sample holder, and an external application device is used.

The application unit applies a predetermined voltage to the blood sample at the set measurement intervals from the starting point at the time when a command to start measurement is received, or at the time when power is applied to blood condition analysis device 1.

The number of electrodes or the material forming the electrodes used as a part of the application unit are not particularly limited as long as the effects of the present technology are not impaired, and any number of electrodes may be formed using any material. Examples thereof include titanium, aluminum, stainless steel, platinum, gold, copper, and graphite. In the present technology, among them, it is particularly preferable to form the electrodes from an electrically conductive material containing titanium. This is because titanium has the property of low coagulant activity on blood.

The measurement unit 15 may also perform several types of measurement. Examples of methods for performing several types of measurement include a method in which several measurement units 15 are provided to perform several types of measurement at the same time, a method in which one measurement unit 15 scans the sample to perform several types of measurement, a method in which the blood sample holder is moved to perform several types of measurement, and a method in which several measurement units 15 are provided, and one or more measurement units 15 to actually perform measurement are selected by switching.

(6) Storage Unit 16

The blood condition analysis device 1 according to the present technology may include a storage unit 16 for storing the drug dosage determined by the drug dosage determination unit 111, the drug concentration detected by the drug concentration detection unit 12, the evaluation results from the blood coagulation evaluation unit 14 and/or the erythrocyte quantitative evaluation unit 13, the measurement results from the measurement unit 15, and the like. In the blood condition analysis device 1 according to the present technology, the storage unit 16 is not indispensable, and it is also possible to connect an external storage device and store the results.

In the blood condition analysis device 1 according to the present technology, separate storage units 16 may be provided for every unit, and it is also possible that one storage unit 16 is designed to store various results from each unit.

(7) Blood Sample

In the blood condition analysis device 1 according to the present technology, the blood sample to be measured is not particularly limited as long as it is a sample containing blood, and may be freely selected. Specific examples of blood samples include whole blood, diluted whole blood, and blood samples having added thereto a drug other than those described above.

(8) Blood Condition Analysis Flow Using Blood Condition Analysis Device 1

Figure 2:
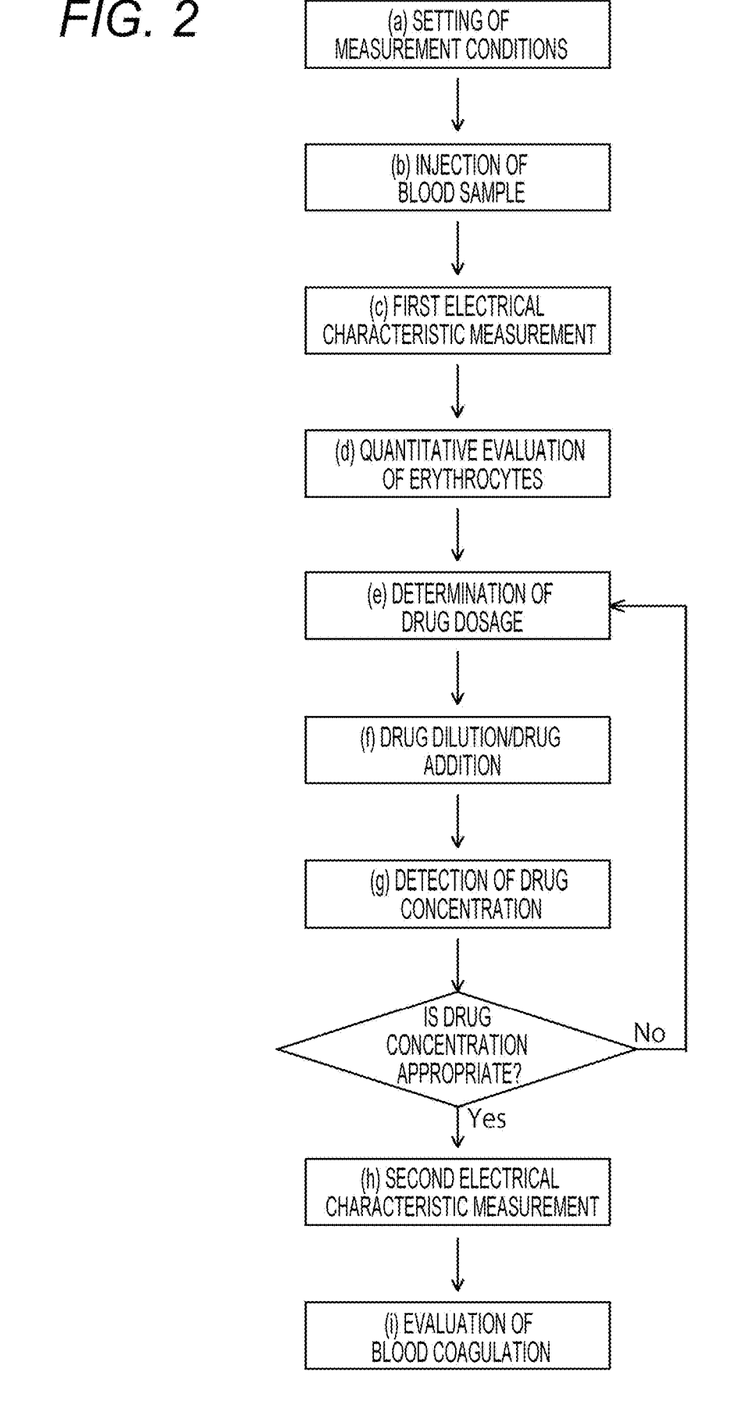
FIG. 2 is a flow chart showing an example of the blood condition analysis flow using the blood condition analysis device 1 according to the present technology.

FIG. 2 is a flow chart showing an example of the blood condition analysis flow using the blood condition analysis device 1 according to the present technology. The following example is a case where the analysis is performed using the blood condition analysis device 1 including a drug dosage control unit 11 (a drug dosage determination unit 111, a drug dilution unit 112), a drug concentration detection unit 12, an erythrocyte quantitative evaluation unit 13, a blood coagulation evaluation unit 14, and a measurement unit 15.

(a) Setting of Measurement Conditions

Measurement conditions, such as the measurement frequency, are set to the measurement unit 15 of the device 1. For example, measurement conditions including the frequency for the quantitative evaluation of erythrocytes, the frequency for the evaluation of blood coagulation, and the like can each be set. In addition, as described above, it is also possible to provide several measurement units 15. In that case, measurement conditions may be set to each measurement unit 15 according to each purpose of measurement.

In the setting of conditions, the user may set each measurement frequency in detail, for example. However, it is also possible that the optimal conditions corresponding to the evaluation items are previously stored in the measurement unit 15 so that the conditions are automatically set simply by the user selecting the target evaluation item.

(b) Injection of Blood Sample

A blood sample is injected into the measurement unit 15. In the case where several measurement units 15 are provided, the blood sample is dispensed into each measurement unit 15. Incidentally, the order of the setting of measurement conditions (a) and the injection of a blood sample (b) is not particularly limited, and it is possible to inject a blood sample after setting the measurement conditions, or it is also possible to set the measurement conditions after injecting a blood sample.

The injection of a blood sample may be performed by the user, but it is also possible that the device is provided with a pipetter and a chip to be mounted on its end so that the device automatically performs the injection.

(c) First Electrical Characteristic Measurement for Quantitative Evaluation of Erythrocytes After the setting of measurement conditions (a) and the injection of a blood sample (b), first, in the measurement unit 15, an electrical characteristic is measured for the quantitative evaluation of erythrocytes. As described above, as the electrical characteristic used for the quantitative evaluation of erythrocytes, electrical characteristics at any frequency are usable.

(d) Quantitative Evaluation of Erythrocytes

Next, in the erythrocyte quantitative evaluation unit 13, the hematocrit and/or hemoglobin content is evaluated on the basis of the electrical characteristic obtained in the first electrical characteristic measurement (c). In the blood condition analysis device 1 according to the present technology, the results of the first electrical characteristic measurement by the measurement unit 15 are automatically transmitted to the erythrocyte quantitative evaluation unit 13, and, in the erythrocyte quantitative evaluation unit 13, the hematocrit and/or hemoglobin content is automatically evaluated on the basis of the received electrical characteristic.

(e) Determination of Drug Dosage

Next, in the drug dosage determination unit 111 of the drug dosage control unit 11, the drug dosage to be added to the blood sample is determined on the basis of the hematocrit and/or hemoglobin content obtained in the quantitative evaluation of erythrocytes (d). In the blood condition analysis device 1 according to the present technology, the hematocrit and/or hemoglobin content evaluated by the erythrocyte quantitative evaluation unit 13 is automatically transmitted to the drug dosage determination unit 111, and, in the drug dosage determination unit 111, the drug dosage to be added to the blood sample is automatically determined on the basis of the received hematocrit and/or hemoglobin content.

More specifically, for example, on the basis of the received hematocrit and/or hemoglobin content, it is possible to employ a method in which the amount of blood plasma is calculated from the hematocrit and/or hemoglobin content, and the drug dosage determination unit 111 automatically determines the drug dosage corresponding to the calculated amount of blood plasma so as to provide the effective amount of drug optimal for the kind of drug or the blood condition to be evaluated.

(f) Drug Dilution/Drug Addition

Next, on the basis of the drug dosage obtained in the determination of the drug dosage (e), the drug is diluted by the drug dilution unit 112 of the drug dosage control unit 11. In the blood condition analysis device 1 according to the present technology, the drug dosage determined by the drug dosage determination unit 111 is automatically transmitted to the drug dilution unit 112, and, in the drug dilution unit 112, the drug is automatically diluted according to the received drug dosage and the concentration of the drug solution to be used.

In the blood condition analysis device 1 according to the present technology, for example, a certain amount of drug is injected from a drug storage unit to a blood sample, and, at the same time, a diluent is injected from the drug dilution unit 112. Accordingly, the dilution of the drug and the addition of the drug to the blood sample are automatically performed. Incidentally, in the case where several measurement units 15 are provided, and the first electrical characteristic measurement for the quantitative evaluation of erythrocytes (c) and the second electrical characteristic measurement for the evaluation of blood coagulation (h) described below are performed by separate measurement units 15, the drug is added to the blood sample dispensed to the measurement unit 15 that performs the second electrical characteristic measurement for the evaluation of blood coagulation (h).

(g) Detection of Drug Concentration

Immediately before the diluted drug is added to the blood sample, the drug concentration is detected by the drug concentration detection unit 12. As a result of the detection of the drug concentration, in the case where the drug concentration is appropriate, the process moves to the second electrical characteristic measurement described below. Conversely, in the case where the drug concentration is not appropriate, the detected drug concentration results are sent to the drug dosage determination unit 111, and the amount of drug to be added or the amount of diluent for dilution is determined again. Then, the drug dilution/drug addition (f) is performed on the basis of the determined amount of drug or diluent.

Alternatively, the setting may also be such that in the case where a certain drug concentration standard is not met, the blood sample is automatically discarded as immeasurable.

Like this, in the blood condition analysis device 1 according to the present technology, measurement errors in the measurement results caused by the variation of the effective drug concentration are previously prevented by controlling the amount (concentration) of drug added, or when the amount of drug added is not suitable for measurement, such blood samples are previously eliminated. As a result, the measurement accuracy can be improved.

(h) Second Electrical Characteristic Measurement for Evaluation of Blood Coagulation In the measurement unit 15, with respect to a blood sample having added thereto an optimum amount of drug, an electrical characteristic is measured for the evaluation of blood coagulation. As described above, as the electrical characteristic used for the evaluation of blood coagulation, electrical characteristics at any frequency are usable.

(i) Evaluation of Blood Coagulation

Next, in the blood coagulation evaluation unit 14, blood coagulation is evaluated on the basis of the electrical characteristic obtained in the second electrical characteristic measurement (h). In the blood condition analysis device 1 according to the present technology, the results of the first electrical characteristic measurement by the measurement unit 15 are automatically transmitted to the blood coagulation evaluation unit 14, and, in the blood coagulation evaluation unit 14, the degree of blood coagulation is automatically evaluated on the basis of the received electrical characteristic.

As described above, in the blood condition analysis device 1 according to the present technology, the effective drug concentration in a blood sample is controlled to an optimum concentration by the drug dosage control unit 11. Therefore, with measurement errors caused by the variation of the effective drug concentration being previously eliminated, various types of evaluation, such as the evaluation of blood coagulation, can be performed.

2. Blood Condition Analysis System 10

Figure 3:
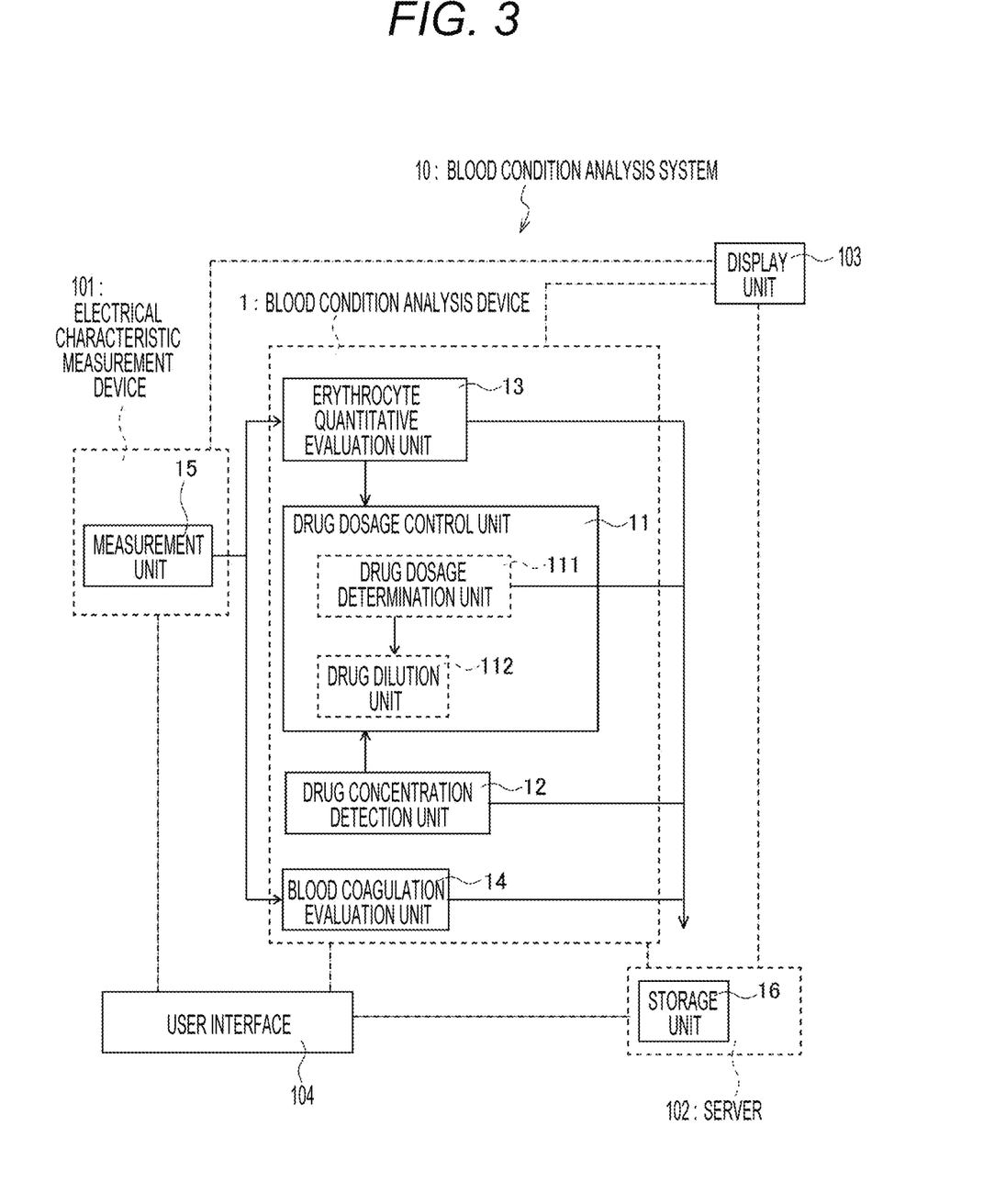
FIG. 3 is a schematic diagram schematically showing the concept of a blood condition analysis system 10 according to the present technology.

FIG. 3 is a schematic diagram schematically showing the concept of a blood condition analysis system 10 according to the present technology. The blood condition analysis system 10 according to the present technology roughly includes at least an electrical characteristic measurement device 101 and a blood condition analysis device 1. Further, as necessary, the system 10 may also include a server 102, a display unit 103, a user interface 104, and the like. Hereinafter, each unit will be described in detail.

(1) Electrical Characteristic Measurement Device 101

The electrical characteristic measurement device 101 includes a measurement unit 15 for measuring an electrical characteristic of a blood sample. The details of the measurement unit 15 are the same as the measurement unit 15 in the blood condition analysis device 1 described above.

(2) Blood Condition Analysis Device 1

The blood condition analysis device 1 is a device for analyzing the condition of the blood sample having added thereto the drug, and includes at least a drug dosage control unit 11. In addition, as necessary, the device may also include a drug dosage determination unit 111, a drug dilution unit 112, a drug concentration detection unit 12, an erythrocyte quantitative evaluation unit 13, a blood coagulation evaluation unit 14, a measurement unit 15, a storage unit 16, and the like. Incidentally, the units included in the blood condition analysis device 1 are the same as the details of the blood condition analysis device 1 described above.

(3) Server 102

The server 102 includes the storage unit 16 for storing the measurement results from the electrical characteristic measurement device 101 and/or the analysis results from the blood condition analysis device 1. The details of the storage unit 16 are the same as the storage unit 16 in the blood condition analysis device 1 described above.

(4) Display Unit 103

The display unit 103 displays the drug dosage determined by the drug dosage determination unit 111, the drug concentration detected by the drug concentration detection unit 12, the evaluation results from the blood coagulation evaluation unit 14 and/or the erythrocyte quantitative evaluation unit 13, the measurement results from the measurement unit 15, and the like. It is possible to provide several display units 103 for every data and results to be displayed, but it is also possible to display all the data and results on one display unit 103.

(5) User Interface 104

The user interface 104 is a unit for the user to perform operation. The user can access each unit of the blood condition analysis system 10 according to the present technology through the user interface 104.

In the blood condition analysis system 10 according to the present technology described above, the electrical characteristic measurement device 101, the blood condition analysis device 1, the server 102, the display unit 103, and the user interface 104 may be mutually connected through a network.

3. Blood Condition Analysis Method

Figure 4:
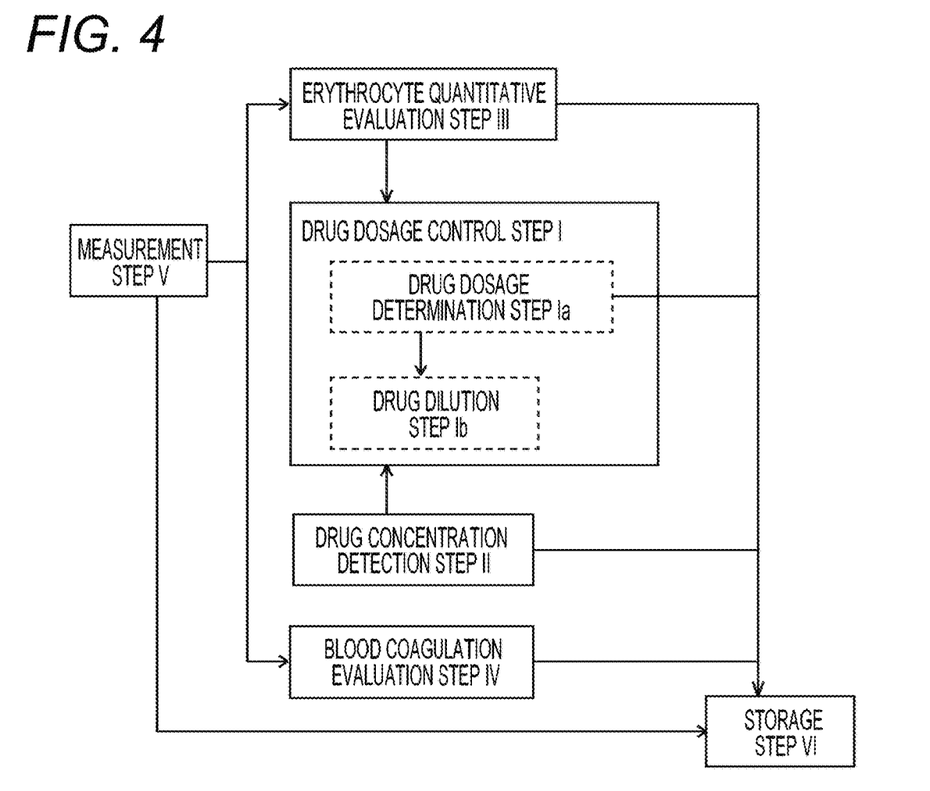
FIG. 4 is a flowchart of a blood condition analysis method according to the present technology.

FIG. 4 is a flowchart of a blood condition analysis method according to the present technology. The blood condition analysis method according to the present technology is a method for analyzing the condition of the blood sample having added thereto the drug, and includes at least a drug dosage control step I. In addition, as necessary, the method may also include a drug concentration detection step II, an erythrocyte quantitative evaluation step III, a blood coagulation evaluation step IV, a measurement step V, a storage step VI, and the like. Hereinafter, each step will be described in detail.

(1) Drug Dosage Control Step I

In the drug dosage control step I, on the basis of the hematocrit and/or hemoglobin content of a blood sample, the dosage of the drug to be added to the blood sample is controlled. In the drug dosage control step I, a drug dosage determination step Ia and/or a drug dilution step Ib may be performed. The details of the control method performed in the drug dosage control step I are the same as the control method executed by the drug dosage control unit 11 of the blood condition analysis device 1 described above.

(2) Drug Concentration Detection Step II

In the drug concentration detection step II, the concentration of the drug to be added to the blood sample is detected. In the blood condition analysis method according to the present technology, the effective concentration of the drug in the blood sample is controlled to be the optimum density in the drug dosage control step I, and thus the drug concentration detection step II is not indispensable. However, when the drug concentration detection step II is provided, and the actual concentration of the drug to be added to the blood sample is checked, the measurement accuracy can be further improved. The details of the detection method performed in the drug concentration detection step II are the same as the detection method executed by the drug concentration detection unit 12 of the blood condition analysis device 1 described above.

(3) Erythrocyte Quantitative Evaluation Step III

In the erythrocyte quantitative evaluation step III, the hematocrit and/or hemoglobin content is evaluated on the basis of an electrical characteristic of the blood sample. This erythrocyte quantitative evaluation step III is not indispensable in the blood condition analysis method according to the present technology. For example, it is also possible that the hematocrit and/or hemoglobin content of the blood sample is previously measured by a different device or method. The details of the evaluation method performed in the erythrocyte quantitative evaluation step III are the same as the evaluation method executed by the erythrocyte quantitative evaluation unit 13 of the blood condition analysis device 1 described above.

(4) Blood Coagulation Evaluation Step IV

In the blood coagulation evaluation step IV, the degree of blood coagulation is evaluated on the basis of an electrical characteristic of the blood sample to give the blood coagulation evaluation results. The blood coagulation evaluation step IV is not indispensable in the blood condition analysis method according to the present technology. For example, it is also possible that the blood coagulation evaluation results are previously obtained by a different device or method. The details of the evaluation method performed in the blood coagulation evaluation step IV are the same as the evaluation method executed by the blood coagulation evaluation unit 14 of the blood condition analysis device 1 described above.

(5) Measurement Step V

In the measurement step V, an electrical characteristic of the blood sample is measured. In the blood condition analysis method according to the present technology, the measurement step V is not indispensable, and it is also possible to use data measured using a different electrical characteristic measurement method or the like. The details of the measurement method performed in the measurement step V are the same as the measurement method executed by the measurement unit 15 of the blood condition analysis device 1 described above.

(6) Storage Step VI

In the storage step VI, the drug dosage determined in the drug dosage determination step Ia, the drug concentration detected in the drug concentration detection step II, the evaluation results from the erythrocyte quantitative evaluation step III and/or the blood coagulation evaluation step IV, the measurement results from the measurement step V, and the like are stored. In the blood condition analysis method according to the present technology, the storage step VI is not indispensable, and it is also possible to analyze the results each time without storing. The details of the storage method performed in the storage step VI are the same as the storage method executed by the storage unit 16 of the blood condition analysis device 1 described above.

4. Blood Condition Analysis Program

The blood condition analysis program according to the present technology is a program for use in the analysis of the condition of the blood sample having added thereto the drug. The blood condition analysis program causes a computer to implement a drug dosage control function of controlling the dosage of the drug to be added to the blood sample on the basis of the hematocrit and/or hemoglobin content of the blood sample. In addition, as necessary, the program may also cause a computer to implement a drug dosage determination function, a drug dilution function, a drug concentration detection function, an erythrocyte quantitative evaluation function, a blood coagulation evaluation function, a measurement function, a storage function, and the like.

In other words, the blood condition analysis program according to the present technology is a program for causing a computer to implement the blood condition analysis method according to the present technology described above. Therefore, the details of each function are the same as each step of the blood condition analysis method described above. Therefore, the description thereof is omitted herein.

Example 1

Hereinafter, the present invention will be described in further detail on the basis of the Examples. Incidentally, the examples described hereinafter show some of typical examples of the present invention, and do not narrow the interpretation of the scope of the present invention.

In Example 1, the correlation between the drug concentration in blood plasma as a blood sample and a blood coagulation ability parameter obtained from an electrical characteristic of the blood sample was examined. Incidentally, in this example, permittivity was used as an example of an electrical characteristic of the blood sample.

[Experiment Method]

(1) Preparation of Hematocrit of Blood Sample

The venous blood of a healthy individual was collected using a vacuum blood collection tube (blood collection amount: 1.8 mL, four tubes) containing citric acid. First one tube was not used and discarded, and the remaining three tubes were centrifuged under mild conditions (300 g×10 minutes) to precipitate erythrocytes on the bottom of each blood collection tube. Part of the supernatant was collected from one blood collection tube and added to another blood collection tube. Next, in each blood collection tube, erythrocytes were uniformly dispersed by restirring. In this manner, blood samples having different hematocrits were prepared (three tubes X two sets).

The hematocrit of each blood sample was measured using a multiparameter automated hematology analyzer (manufactured by Sysmex Corporation). Incidentally, the hematocrit can also be evaluated using an electrical characteristic, such as permittivity. Therefore, as in the evaluation of blood coagulation described below, by using an electrical characteristic, a similar experiment/evaluation can be performed without separately performing the measurement for determining the hematocrit.

(2) Addition of Drug

With respect to one set of each blood sample prepared above, 2.4 µmol of calcium chloride was added to all the blood samples (reagent-amount-unadjusted samples). With respect to the other set, the amounts of calcium chloride shown in the following Table 2 were prepared and added to the respective blood samples to make the effective drug concentration constant (reagent-amount-adjusted samples).

TABLE 2

| | Reagent-amount-unadjusted sample | | | Reagent-amount-adjusted sample | | |
|---|---|---|---|---|---|---|
| Hematocrit | 25.70% | 29.70% | 52.50% | 25.70% | 29.70% | 52.50% |
| Amount of blood used | 180 µL | 180 µL | 180 µL | 180 µL | 180 µL | 180 µL |
| Amount of reagent added | 2.4 µmol | 2.4 µmol | 2.4 µmol | 2.8 µmol | 2.7 µmol | 1.9 µmol |
| Effective reagent concentration | 15.6 mM | 16.3 mM | 22.7 mM | 18.5 mM | 18.5 mM | 18.5 mM |

(3) Measurement of Electrical Characteristic

An aqueous calcium chloride solution was added to each of the blood samples prepared above to start the blood coagulation reaction. Immediately after the start, the permittivity was measured at a temperature of 37° C. and a frequency region of 10 MHz.

[Results]

Figure 5:
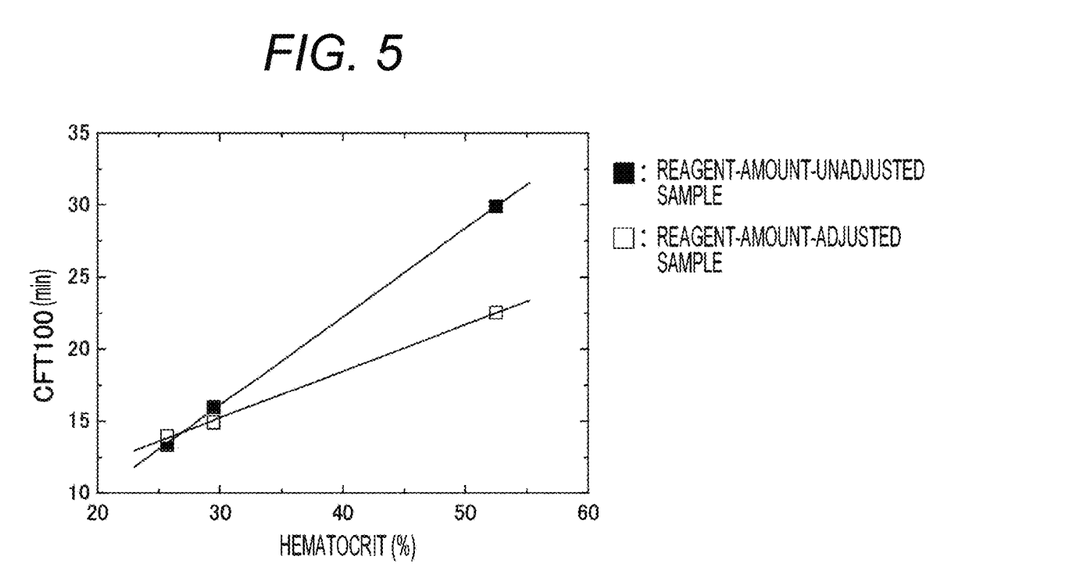
FIG. 5 is a graph as a substitute for a drawing, showing the correlation between the blood coagulation time (CFT100) determined by permittivity measurement and the hematocrit in Example 1.

FIG. 5 shows the correlation between the blood coagulation time (CFT100) determined by permittivity measurement and the hematocrit. As shown in FIG. 5, in both cases where the amount (concentration) of reagent was adjusted and not adjusted, the coagulation time increased with an increase in hematocrit. However, the amount of change was obviously greater in the reagent-amount-unadjusted samples. From the results, it turned out that the coagulation time varies not only with the hematocrit itself but also with the effective concentration of the reagent. It also turned out that when the effective drug concentration in a blood sample is prepared by adjusting the amount of reagent added on the basis of the hematocrit, artifacts caused by the variation of the effective drug concentration can be reduced.

Incidentally, this technology may also be configured as follows.

(1)

A blood condition analysis device, for analyzing the condition of a blood sample having added thereto at least one kind of drug selected from the group consisting of anticoagulation treatment canceling agents, coagulation activators, anticoagulants, platelet activators, and antiplatelet agents, the device including a drug dosage control unit for controlling the dosage of the drug to be added to the blood sample on the basis of the hematocrit and/or hemoglobin content of the blood sample.

(2)
The blood condition analysis device according to (1), wherein the drug dosage control unit includes a drug dosage determination unit for determining the dosage of the drug to be added to the blood sample on the basis of the hematocrit and/or hemoglobin content of the blood sample.

(3)
The blood condition analysis device according to (1) or (2), wherein the drug dosage control unit includes a drug dilution unit for diluting the drug.

(4)
The blood condition analysis device according to (2), including a drug dilution unit for diluting the drug on the basis of the dosage determined by the drug dosage determination unit.

(5)
The blood condition analysis device according to any of (1) to (4), including a drug concentration detection unit for detecting the concentration of the drug to be added to the blood sample.

(6)
The blood condition analysis device according to any of (1) to (5), including an erythrocyte quantitative evaluation unit for determining the hematocrit and/or hemoglobin content on the basis of an electrical characteristic of the blood sample.

(7)
The blood condition analysis device according to any of (1) to (6), including a blood coagulation evaluation unit for evaluating the degree of blood coagulation on the basis of an electrical characteristic of the blood sample.

(8)
The blood condition analysis device according to any of (1) to (7), including a measurement unit for measuring electrical characteristics of the blood sample.

(9)
The blood condition analysis device according to (8), including:
an erythrocyte quantitative evaluation unit for determining the hematocrit and/or hemoglobin content on the basis of an electrical characteristic of the blood sample; and
a blood coagulation evaluation unit for evaluating the degree of blood coagulation on the basis of an electrical characteristic of the blood sample.

(10)
A blood condition analysis system, including:
an electrical characteristic measurement device including a measurement unit for measuring electrical characteristics of a blood sample; and
a blood condition analysis device for analyzing the condition of the blood sample having added thereto at least one kind of drug selected from the group consisting of anticoagulation treatment canceling agents, coagulation activators, anticoagulants, platelet activators, and antiplatelet agents, the device including a drug dosage control unit for controlling the dosage of the drug to be added to the blood sample on the basis of the hematocrit and/or hemoglobin content of the blood sample.

(11)
The blood condition analysis system according to (10), including a server for storing measurement results from the electrical characteristic measurement device and/or analysis results from the blood condition analysis device.

(12)
The blood condition analysis system according to (11), wherein the server is connected to the electrical characteristic measurement device and/or the blood condition analysis device through a network.

(13)
A blood condition analysis method, for analyzing the condition of a blood sample having added thereto at least one kind of drug selected from the group consisting of anticoagulation treatment canceling agents, coagulation activators, anticoagulants, platelet activators, and antiplatelet agents,
the method including a drug dosage control step of controlling the dosage of the drug to be added to the blood sample on the basis of the hematocrit and/or hemoglobin content of the blood sample.

(14)
A blood condition analysis program, for use in the analysis of the condition of a blood sample having added thereto at least one kind of drug selected from the group consisting of anticoagulation treatment canceling agents, coagulation activators, anticoagulants, platelet activators, and antiplatelet agents,
the program causing a computer to implement a drug dosage control function of controlling the dosage of the drug to be added to the blood sample on the basis of the hematocrit and/or hemoglobin content of the blood sample.

REFERENCE SIGNS LIST

1 Blood condition analysis device
11 Drug dosage control unit
111 Drug dosage determination unit
112 Drug dilution unit
12 Drug concentration detection unit
13 Erythrocyte quantitative evaluation unit
14 Blood coagulation evaluation unit
15 Measurement unit
16 Storage unit
10 Blood condition analysis system
101 Electrical characteristic measurement device
102 Server
103 Display unit
104 User interface
I Drug dosage control step
Ia Drug dosage determination step
Ib Drug dilution step
II Drug concentration detection step
III Erythrocyte quantitative evaluation step
IV Blood coagulation evaluation step
V Measurement step
VI Storage step

The invention claimed is:
1. A blood condition analysis device for analyzing the condition of a blood sample having added thereto at least one kind of drug selected from the group consisting of anticoagulation treatment canceling agents, coagulation activators, anticoagulants, platelet activators, and antiplatelet agents,
the device comprising a drug dosage control unit for controlling the dosage of the drug to be added to the blood sample on the basis of the hematocrit and/or hemoglobin content of the blood sample, and
a drug concentration detection unit for detecting the concentration of the drug to be added to the blood sample and for determining if the concentration is correct.

2. The blood condition analysis device according to claim 1, wherein the drug dosage control unit includes a drug dosage determination unit for determining the dosage of the drug to be added to the blood sample on the basis of the hematocrit and/or hemoglobin content of the blood sample.

3. The blood condition analysis device according to claim 1, wherein the drug dosage control unit includes a drug dilution unit for diluting the drug.

4. The blood condition analysis device according to claim 2, further comprising a drug dilution unit for diluting the drug on the basis of the dosage determined by the drug dosage determination unit.

5. The blood condition analysis device according to claim 1, further comprising an erythrocyte quantitative evaluation unit for determining the hematocrit and/or hemoglobin content on the basis of an electrical characteristic of the blood sample.

6. The blood condition analysis device according to claim 1, further comprising a blood coagulation evaluation unit for evaluating the degree of blood coagulation on the basis of an electrical characteristic of the blood sample.

7. The blood condition analysis device according to claim 1, further comprising a measurement unit for measuring electrical characteristics of the blood sample.

8. The blood condition analysis device according to claim 7, further comprising:
  an erythrocyte quantitative evaluation unit for determining the hematocrit and/or hemoglobin content on the basis of an electrical characteristic of the blood sample; and
  a blood coagulation evaluation unit for evaluating the degree of blood coagulation on the basis of an electrical characteristic of the blood sample.

9. A blood condition analysis system, comprising:
  an electrical characteristic measurement device including a measurement unit for measuring electrical characteristics of a blood sample; and
  a blood condition analysis device for analyzing the condition of the blood sample having added thereto at least one kind of drug selected from the group consisting of anticoagulation treatment canceling agents, coagulation activators, anticoagulants, platelet activators, and antiplatelet agents, the device including a drug dosage control unit for controlling the dosage of the drug to be added to the blood sample on the basis of the hematocrit and/or hemoglobin content of the blood sample, and
  a drug concentration detection unit for detecting the concentration of the drug to be added to the blood sample and for determining if the concentration is correct.

10. The blood condition analysis system according to claim 9, further comprising a server for storing measurement results from the electrical characteristic measurement device and/or analysis results from the blood condition analysis device.

11. The blood condition analysis system according to claim 10, wherein the server is connected to the electrical characteristic measurement device and/or the blood condition analysis device through a network.

12. A blood condition analysis method for analyzing the condition of a blood sample having added thereto at least one kind of drug selected from the group consisting of anticoagulation treatment canceling agents, coagulation activators, anticoagulants, platelet activators, and antiplatelet agents,
  the method comprising a drug dosage control step of controlling the dosage of the drug to be added to the blood sample on the basis of the hematocrit and/or hemoglobin content of the blood sample, and
  a drug concentration detection step for detecting the concentration of the drug to be added to the blood sample and for determining if the concentration is correct.

13. A blood condition analysis program for use in the analysis of the condition of a blood sample having added thereto at least one kind of drug selected from the group consisting of anticoagulation treatment canceling agents, coagulation activators, anticoagulants, platelet activators, and antiplatelet agents,
  the program causing a computer to implement a drug dosage control function of controlling the dosage of the drug to be added to the blood sample on the basis of the hematocrit and/or hemoglobin content of the blood sample, and
  a drug concentration function for detecting the concentration of the drug to be added to the blood sample for determining if the is correct.

* * * * *